(12) United States Patent
Tucek et al.

(10) Patent No.: US 8,366,756 B2
(45) Date of Patent: Feb. 5, 2013

(54) LOW LEVEL LASER THERAPY DEVICE WITH OPEN BORE

(75) Inventors: Kevin B Tucek, McKinney, TX (US); Jeremy Tucek, McKinney, TX (US); Colby Montgomery, McKinney, TX (US)

(73) Assignee: Erchonia Corporation, McKinney, TX (US)

( * ) Notice: Subject to any disclaimer, the term of this patent is extended or adjusted under 35 U.S.C. 154(b) by 0 days.

(21) Appl. No.: 13/438,490

(22) Filed: Apr. 3, 2012

(65) Prior Publication Data
US 2012/0215289 A1     Aug. 23, 2012

Related U.S. Application Data

(63) Continuation-in-part of application No. 12/870,002, filed on Aug. 27, 2010.

(60) Provisional application No. 61/237,795, filed on Aug. 28, 2009.

(51) Int. Cl.
*A61F 7/00*       (2006.01)
(52) U.S. Cl. ............................................. 607/91; 607/89
(58) Field of Classification Search .............. 607/88–91; 600/410–412, 415, 421
See application file for complete search history.

(56) References Cited

U.S. PATENT DOCUMENTS

| | | | | |
|---|---|---|---|---|
| 7,534,255 | B1 * | 5/2009 | Streeter et al. | 607/88 |
| 7,575,589 | B2 * | 8/2009 | De Taboada et al. | 607/88 |
| 7,850,720 | B2 * | 12/2010 | Shefi et al. | 607/88 |
| 2003/0181961 | A1 * | 9/2003 | Kamei | 607/88 |

FOREIGN PATENT DOCUMENTS

| | | | |
|---|---|---|---|
| EP | 0 130 950 B1 | * | 11/1990 |
| JP | 04023634 | * | 2/1992 |

* cited by examiner

*Primary Examiner* — Ahmed Farah
(74) *Attorney, Agent, or Firm* — Etherton Law Group, LLC; Sandra L. Etherton; Benjamin D. Tietgen

(57) ABSTRACT

A laser device for applying low-level laser energy around a patient's body part comprises a laser support having an open bore through which the body part to be treated is inserted and at least one laser connected to the laser support. Each laser emits laser energy in a plane substantially perpendicular to the axis of the bore, such that energy is applied to the circumference, of the body part, or a portion thereof. The laser support is attached to an adjustable stanchion that is shaped to cantilever the ring so that a chair or table may be positioned underneath the ring. In the preferred embodiment, the laser support is a C-shaped ring having a diameter large enough to accommodate at least a patient's upper arm. Lasers are slidably engaged with the C-ring and can be moved around the circumference of the ring to treat desired locations around the upper arm.

4 Claims, 12 Drawing Sheets

LOW LEVEL LASER THERAPY DEVICE WITH OPEN BORE

CROSS-REFERENCE TO RELATED APPLICATIONS

This application is a continuation-in-part of U.S. patent application Ser. No. 12/870,002 filed Aug. 27, 2010, which is a non-provisional of and claims the benefit of U.S. Provisional patent application No. 61/237,795, filed Aug. 28, 2009.

FIELD OF INVENTION

This invention relates generally to a laser device for treating patients with low-level laser energy. More particularly, this invention relates to a device for treating all sides of a patient's body parts in a reduced treatment time.

BACKGROUND

There is a great demand to contour the body and reduce cellulite. Cellulite is often described as skin with ripples or dimples or as skin having a cottage cheese or orange-peel texture. Cellulite mainly affects women, although some men also suffer from cellulite. Typically, cellulite is most prevalent on patients' thighs, hips and buttocks, but it also can be found on the breasts, lower abdomen and upper arms as well. In an effort to reduce cellulite, many people resort to one of three treatment options: liposuction or similar methods of removing fat, vigorous massage, or cellulite creams. Unfortunately, none of these options have been effective at actually reducing cellulite. Additionally, each of these options requires distinct treatments for each area requiring treatment.

Cellulite is the herniation of superficial and deep fat into the dermis. Latest research suggests that longitudinal fibers or cords of connective tissue fascia, which is comprised of collagen, is progressively weakened by estrogen. The fascia hardens and loses its ability to contain the fat mass that is normally contained in chambers separated by septa of connective tissue. The weakened fascia allows the fat to move upward and push into the dermis. As the connective tissue gives way the fat mass is free to expand, leading to a wavy or dimpled skin appearance commonly called cellulite. Unfortunately, cellulite does not respond well to weight loss, exercise, creams, or surgical liposuction.

In an effort to reduce cellulite, many sufferers try to remove the underlying fat through surgical procedures such as liposuction or through liposuction alternatives. Liposuction involves suctioning excess adipose tissue from the body of a patient. Generally, adipose tissue is connective tissue comprising collagen fibers, reticular fibers, non-cellular material and adipocytes. Adipocytes, the fat cells, are enclosed membranes filled with globules of triglycerides. In normal fat the adipocytes have regular contours and form into grapelike clusters. The intracellular fat is relatively fluid and, if the membrane is pierced, will flow out of the cell into the interstitial space. The interstitial space includes the connective tissue as well as nerves, blood vessels, and lymphatics, among other substances.

While liposuction is effective at removing fat, traditional liposuction has not been effective in reducing cellulite and may actually make the cellulite appear worse. Additionally, traditional liposuction carries undesirable risks and side effects because it involves inserting a narrow tube, or cannula, through a tiny incision in the skin into the subcutaneous fatty tissue and repeatedly pushing and pulling through the fat layer, separating and puncturing the fat cells and suctioning them out. The procedure can damage nerves, lymphatics and vasculature in the surrounding area, often resulting in significant loss of blood as the blood is vacuumed out with the fat and the formation of seroma due to damaged lymphatic channels. In addition, the post-procedure recovery period is long and often accompanied by a great deal of inflammation, bruising and concomitant pain. Finally, each area needing treatment must be treated separately with liposuction.

For the upper arms, another invasive procedure used to reshape the arm to achieve smoother skin and a more toned and proportionate appearance is to surgically remove excess skin and fat between the underarm and the elbow. This procedure is known as an arm lift, or brachioplasty. For it, too, the post-procedure recovery period is long and often accompanied by a great deal of inflammation, bruising and concomitant pain.

Non-invasive methods of reducing fat have also proven ineffective at reducing cellulite. In general, non-invasive methods are preferred because they minimize trauma to the patient, reduce the risk of infection, and speed up recovery time, among other reasons. Such non-invasive methods include subjecting a patient to electromagnetic energy, such as microwave, ultrasound or radio frequency radiation. These procedures are disadvantageous, however, because they utilize such high energy sources that they heat the surrounding tissue, which can result in damage to the tissue and pain. Again, recovery time is significant, and these methods are not effective at reducing cellulite.

A less traumatic non-invasive method of reducing fat is described U.S. Patent Publication 2005/0203594, which discloses the use of low-level laser energy applied externally to the patient to release at least a portion of the intracellular fat into the interstitial space, wherein the released fat and damaged fat cells are removed from the patient's body through one or more of the patient's normal bodily systems.

Low level laser therapy ("LLLT") is used in the treatment of a broad range of conditions. LLLT improves wound healing, reduces edema, and relieves pain of various etiologies, including successful application to wound and surgical sites to reduce inflammation and pain. LLLT is also used in the treatment and repair of injured muscles and tendons. LLLT utilizes low level laser energy, wherein the treatment has a dose rate that causes no immediate detectable temperature rise of the treated tissue and no macroscopically visible changes in tissue structure. Consequently, the treated and surrounding tissue is not heated or damaged, and the patient feels no sensation during treatment. Some LLLT applications have effectively photodestroyed a targeted biological element under suitable treatment conditions. For example, LLLT may be used in fat reduction to create a transitory pore in fat cell walls, through which fat is released into the interstitial space.

There are a number of variables in laser therapy, including the wavelength of the laser beam, the area impinged by the laser beam, the shape of the beam spot when it impinges the area, the power of the laser source, the intensity or fluence of the laser energy, the laser pulse width, and the treatment duration. The setting of these variables typically depends heavily on the tissue characteristics of the specific patient, and the success of each therapy depends on the relationship and combination of these variables. For example, fat reduction may be facilitated with one regimen utilizing a given power, wavelength, and treatment duration, whereas pain may be treated with a regimen utilizing a different wavelength and treatment duration, and inflammation a third regimen. Specific devices may be used for each type of therapy.

Low-level laser therapy devices are conventionally handheld laser-energy emitting devices in which the operator sweeps the device across a patient's body part while the patient rests on a table. Other low-level laser therapy devices known in the art are stationary plates of laser emission sources that treat one side of a patient's body at a given time. No prior art devices enable the application of low-level laser therapy around a body part: the patient has to be turned over and the treatment repeated to treat the yet-untreated portion of patient's body.

Therefore, it would be desirable to have a low-level laser therapy device to treat all sides of a body part with a single treatment. It would also be desirable to reduce treatment time for contouring a patient's body, particularly an area that has a smaller, specific treatment area, such as a patient's upper arm. Therefore, an object of this invention is to provide a low-level laser therapy device having an open bore through which a patient's body part can be inserted for treatment.

SUMMARY OF THE INVENTION

This invention is an apparatus for delivering low-level laser energy to all sides of a body part with a single treatment, especially to the upper arm. The device comprises a plurality of laser energy sources moveably connected to a ring or other support structure having an open bore. The ring is, in turn, attached to an adjustable stanchion that enables the ring to be cantilevered away from the stanchion so that the laser energy sources can be easily positioned closely around a patient's body part. The laser energy sources are oriented to emit light substantially parallel to the plane of the ring and toward the center of the bore. The laser energy sources are in electrical communication with controls housed in the stanchion. An arm rest and a computer interface are also attached to the stanchion. In the preferred embodiment, the laser support is a C-shaped ring having a diameter large enough to accommodate at least a patient's upper arm. Laser energy sources are enclosed in housings which are slidably engaged with the C-ring and can be moved around the circumference of the ring to treat desired locations around the upper arm. The ring tilts towards and away from the stanchion to allow it the ring be positioned appropriately about the body part. Using the preferred embodiment, the patient's upper arm is treated for fat reduction. The patient inserts her arm through the ring so that her forearm rests on the arm rest and her upper arm is surrounded by the ring. The laser energy sources on the ring emit laser energy on the upper arm.

DETAILED DESCRIPTION OF THE INVENTION

Figure 1:
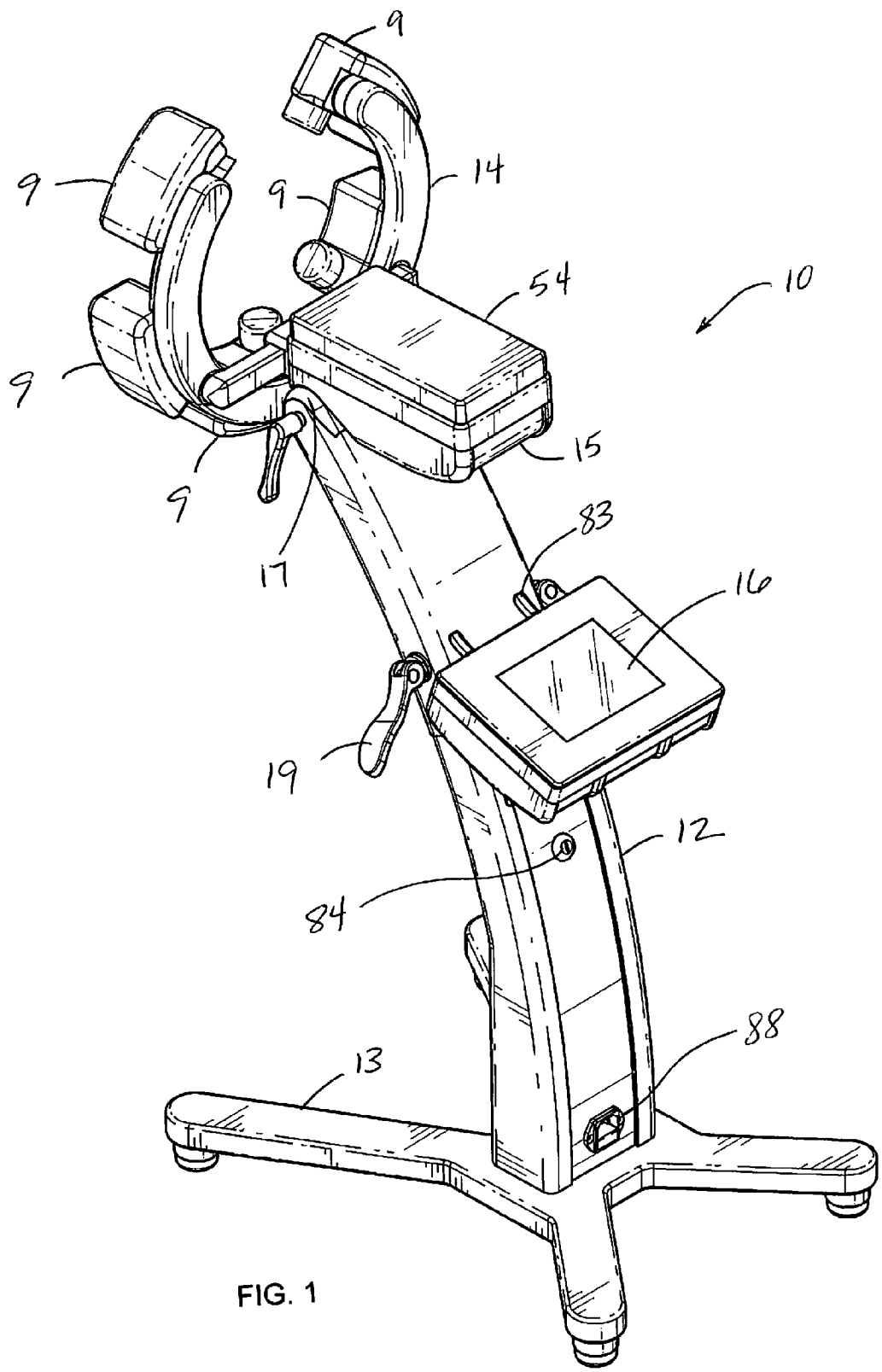
FIG. 1 is a top perspective view of the laser therapy device.

Referring to FIGS. 1-5, the present device, referred to generally as device 10, comprises a laser support 14 having an open bore through which the body part to be treated can be inserted. One or more low-level laser energy sources 11 is connected to the laser support 14, typically by being contained within a laser housing 9 which is directly attached to the laser support 14 using a laser mount 7. The laser support 14 is attached to a stanchion 12. The laser energy sources 11 are controlled electronically and the controls 15 are preferably housed in or attached to the stanchion 12. A computer interface 16 enables the operator to input and receive information about the control and operation of the device 10.

The laser support 14 serves to retain each laser energy source 11 in its desired position over the area of the patient to be treated. The laser support 14 has an open bore to receive part of a patient's body which is to be treated substantially within the bore. The bore is therefore sufficiently large that the patient's body part can be inserted into and through the bore without touching the apparatus. Laser energy can be applied around the body part in one treatment, eliminating the need to turn the patient over to treat the yet-untreated portion of the body part that had been resting on a table. The laser support 14 is preferably made with a fixed bore dimension. For example, if the device 10 is to be used solely for treating upper arms, the device bore can be fixed at dimension large enough to accommodate only upper arms. If the device 10 will be used to treat thighs, the device bore can be fixed at dimension large enough to accommodate thighs which, because thighs are larger than upper arms, will enable the device to also treat upper arms. The laser support 14 may also be made adjustable to reduce and enlarge the size of the bore, so that the device can be adjusted to more closely accommodate different size body parts.

The laser support 14 is moveably attached to the stanchion 12. In the preferred embodiment, the laser support 14 can be moved relative to the stanchion 12 to enable the laser energy sources 11 to be more easily positioned over the desired area to be treated. FIG. 1 illustrates the laser support 14 attached by a hinge 17 to the stanchion 12, which enables the top of the laser support 14 to be rotated in the x direction to and away from the stanchion 12, as shown by the arrow in FIG. 5. The laser support 14 may use other attachment mechanisms to enable the laser support 14 to move relative to the stanchion 12, such as a carriage and carriage rail, ratchet and pawl, or rack and pinion. The laser support's adjustability in combination with the stanchion's adjustability, as discussed in more detail below, enables the laser energy sources 11 to be easily positioned over the desired area to be treated.

Figure 4:
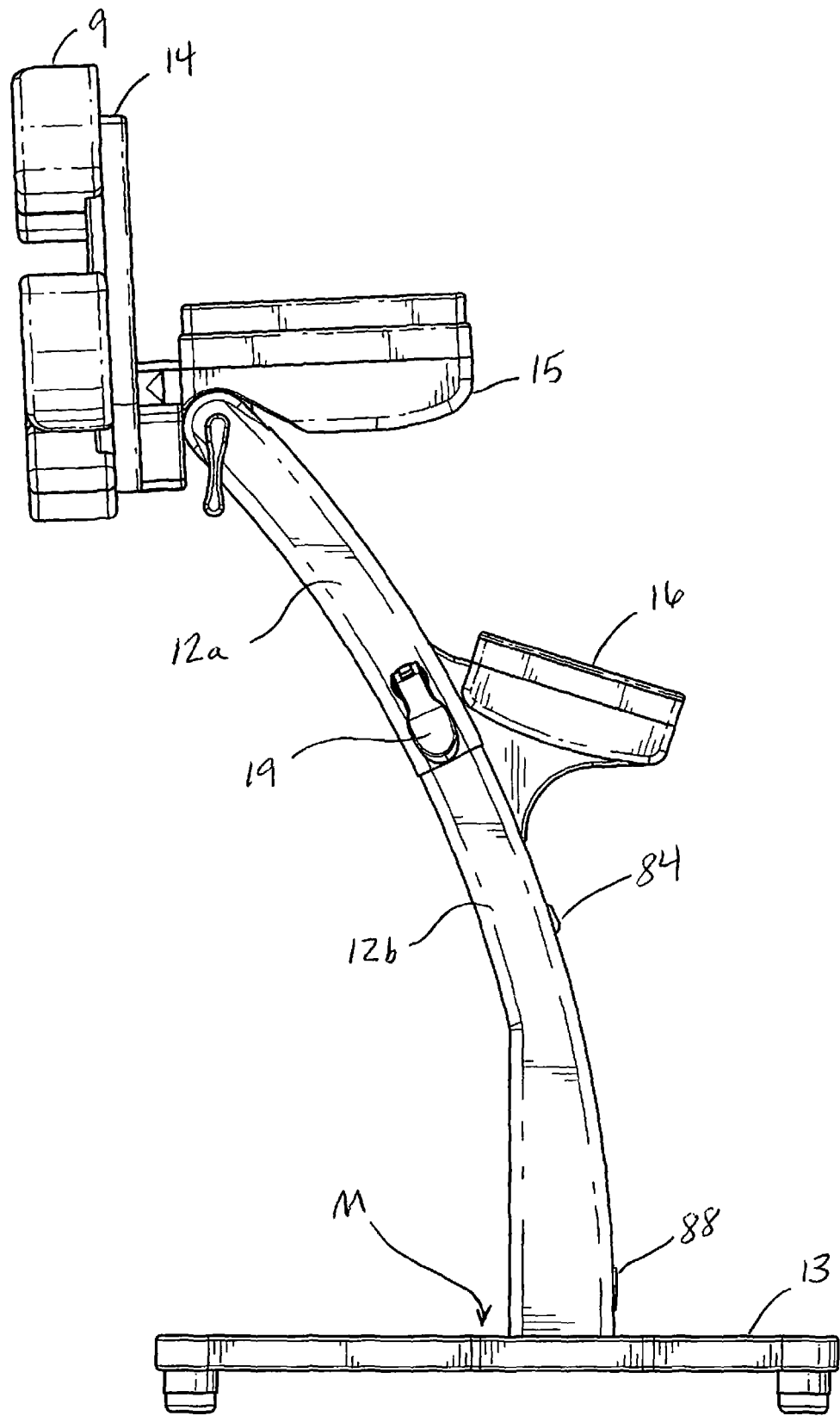
FIG. 4 is a side view of the laser therapy device.

The stanchion 12 is shaped to cantilever the laser support 14 in such a way that, with the stanchion 12 resting on the floor, the laser support 14 can be placed around a patient's body part without bumping the table or chair that the patient is resting on. The chair or table may in some cases be disposed between the laser support 14 and the floor. The stanchion 12 is also adjustable in the y and z directions, or height and location on the floor. FIGS. 1 and 4 show levers 19 that allow the upper portion of the stanchion 12a to be extended from the lower portion of the stanchion 12b. In the preferred embodiment the stanchion 12 is shaped such that extending the upper portion 12a from the lower portion 12b increases the distance the laser support 14 is from the floor and increases its distance from the midpoint M of the stanchion base 13. See FIG. 4. The device 10 is preferably stationary, but is compact enough to be moved from one position to another across the floor by lifting it off the floor. Alternatively, wheels can be attached to the stanchion base 13 to enable the device to be moved across the floor more easily.

Figure 5:
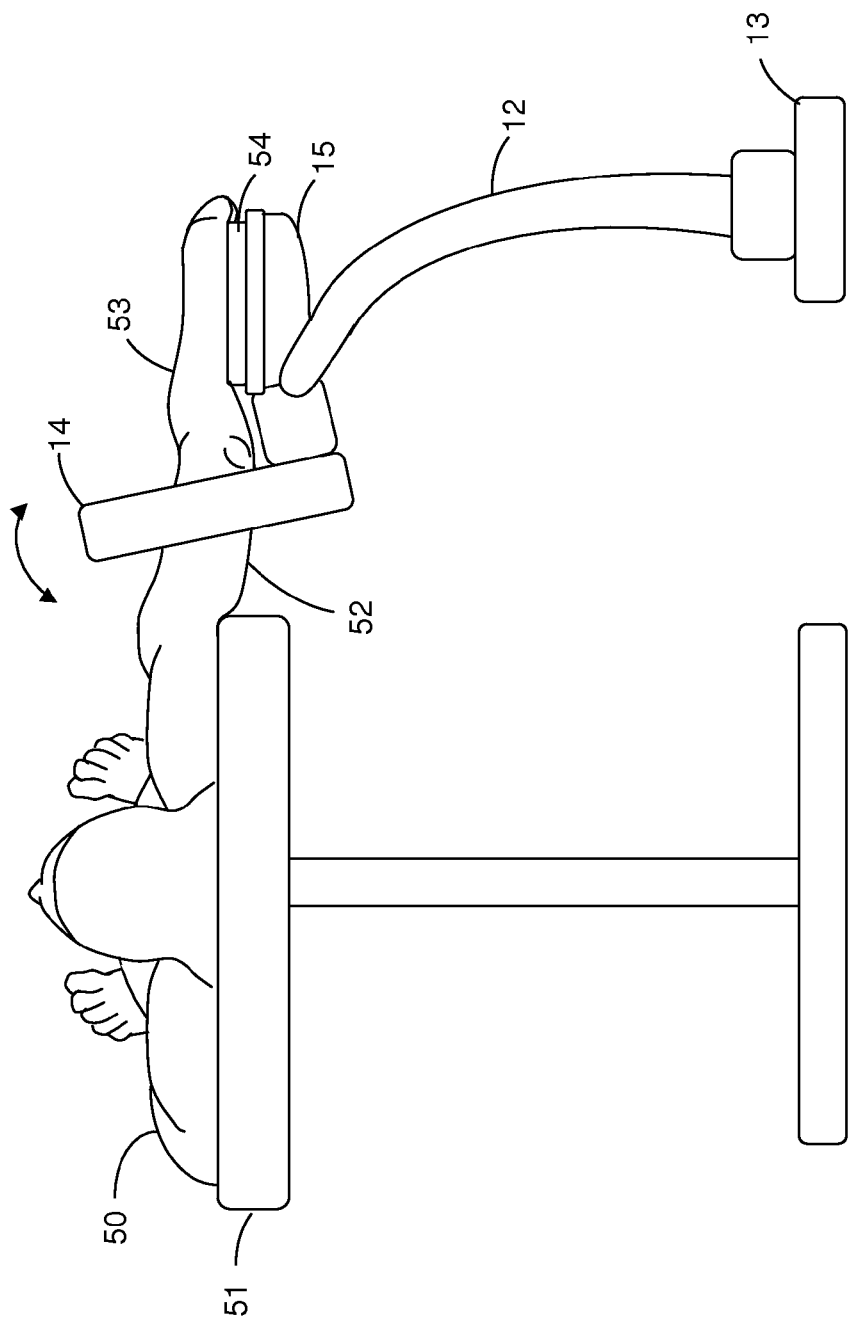
FIG. 5 is an elevation view of a patient lying on a table with her arm inserted through the laser support and her upper arm being treated with laser energy.

FIG. 5 illustrates a patient 50 lying on a table 51 with her arm inserted through the laser support 14 and her upper arm 52 being treated with laser energy. The patient's forearm 53 rests on an arm support 54. By positioning the laser support 14 and the arm support 54 appropriately, the patient's upper arm 52 does not come in contact with the laser support 14 or the laser housings (not shown in FIG. 5.) In this way the laser energy sources do not touch the patient, which has benefits including enabling the operator to see the exact locations where the laser energy is being applied to the patient and enable the laser energy to be projected over a broader area than a laser that touched the skin could achieve. The shape and adjustability of the stanchion 12 enable the laser energy sources 11 to be easily positioned closely around a patient's body part.

Figure 2:
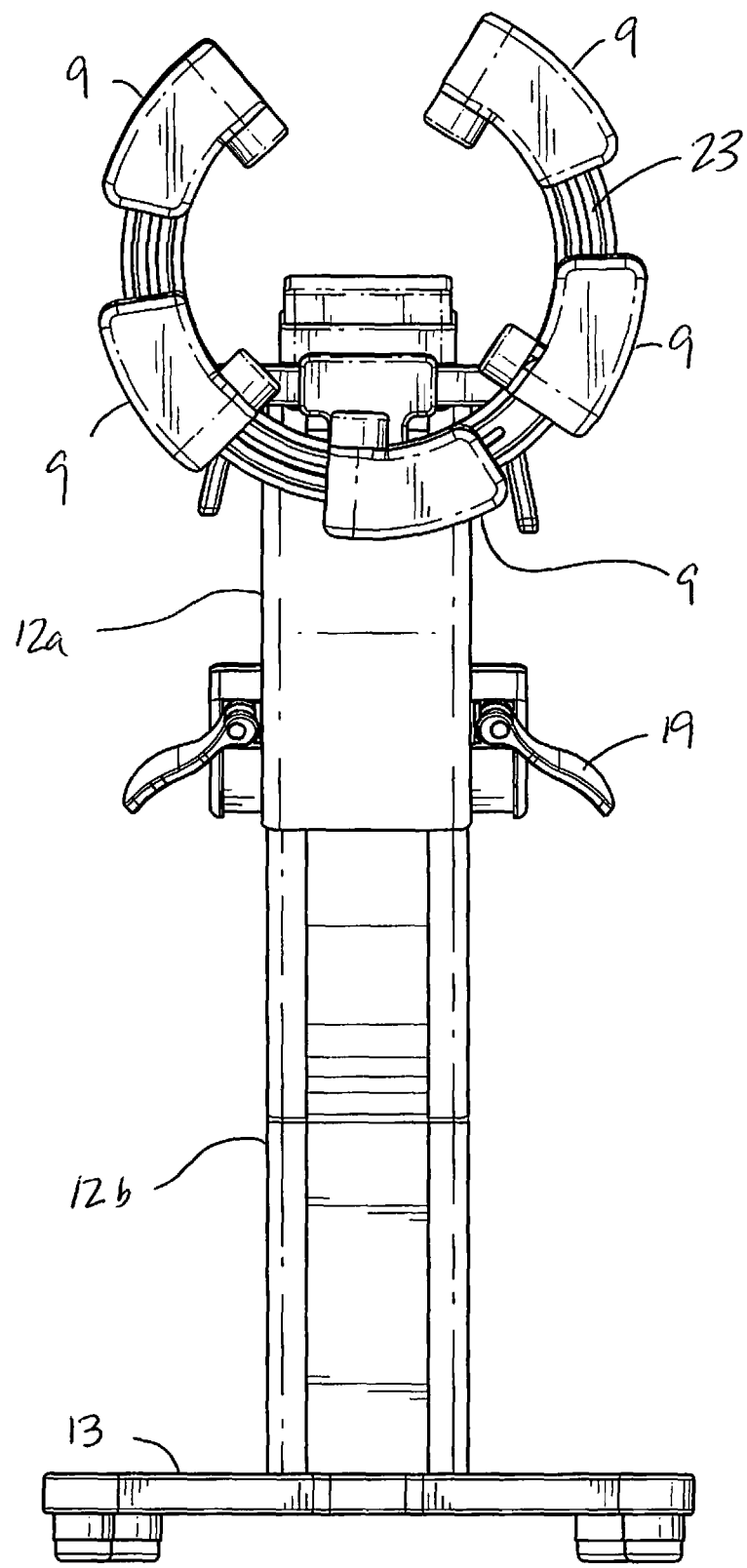
FIG. 2 is an elevation view of the rear of the laser therapy device.
Figure 3A:
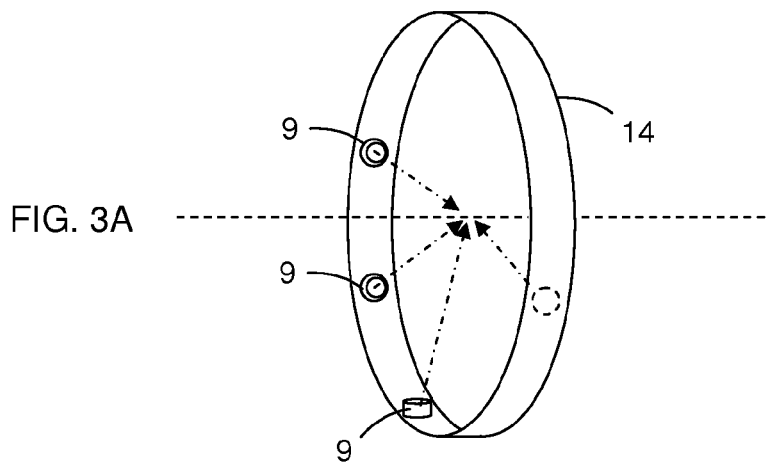
FIG. 3A is a perspective view of a laser support with laser housings attached to the inside surface of the support.
Figure 3B:
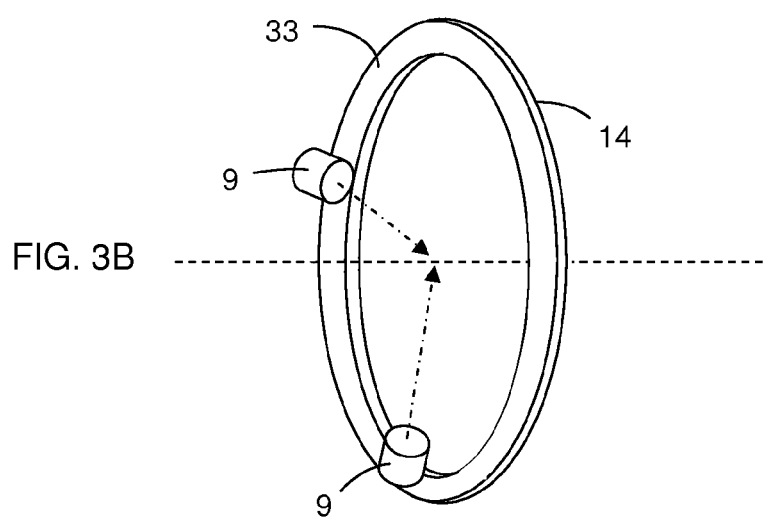
FIG. 3B is a perspective view of another embodiment of the laser support with laser housings attached to the face of the support.
Figure 3C:
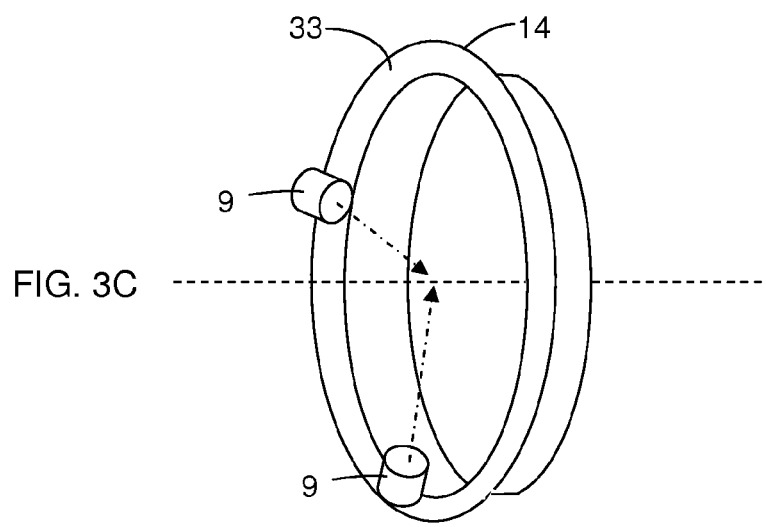
FIG. 3C is a perspective view of yet another embodiment of the laser support with a deeper bore and laser housings attached to the face of the support.

The laser support 14 preferably has a substantially circular bore, although square, oblong, oval, elliptical and bores of other shapes are acceptable. The outside dimension of the laser support 14 is also preferably circular, but may take on other shapes. FIGS. 1 and 2 show a C-shaped laser support with a circular bore. FIGS. 3A-C show a circular laser support with a circular bore. In FIG. 3A, the laser support 14 is a ring with laser housings 9 attached to the inside surface of the ring. FIG. 3B is a ring with a short bore 32 and a face 33 on the ring to which the laser housings 9 are attached. FIG. 3C is yet another embodiment of the laser support 14 with a deeper bore and laser housings 9 attached to the face of the laser support 14. In another embodiment, a laser support 14 has a bore so deep that the laser support 14 takes on the shape of a tube.

Each laser housing 9 houses one or more laser energy sources 11. The laser housings 9 are preferably moveably attached to the laser support 14 using a laser mount 7 such that each laser housing 9 can be moved independently from one position to another around the perimeter of the bore and secured in the desired place. This enables laser energy to be emitted substantially simultaneously around a portion of a patient's body, such as an upper arm, calf, thigh, head or torso.

Figure 11:
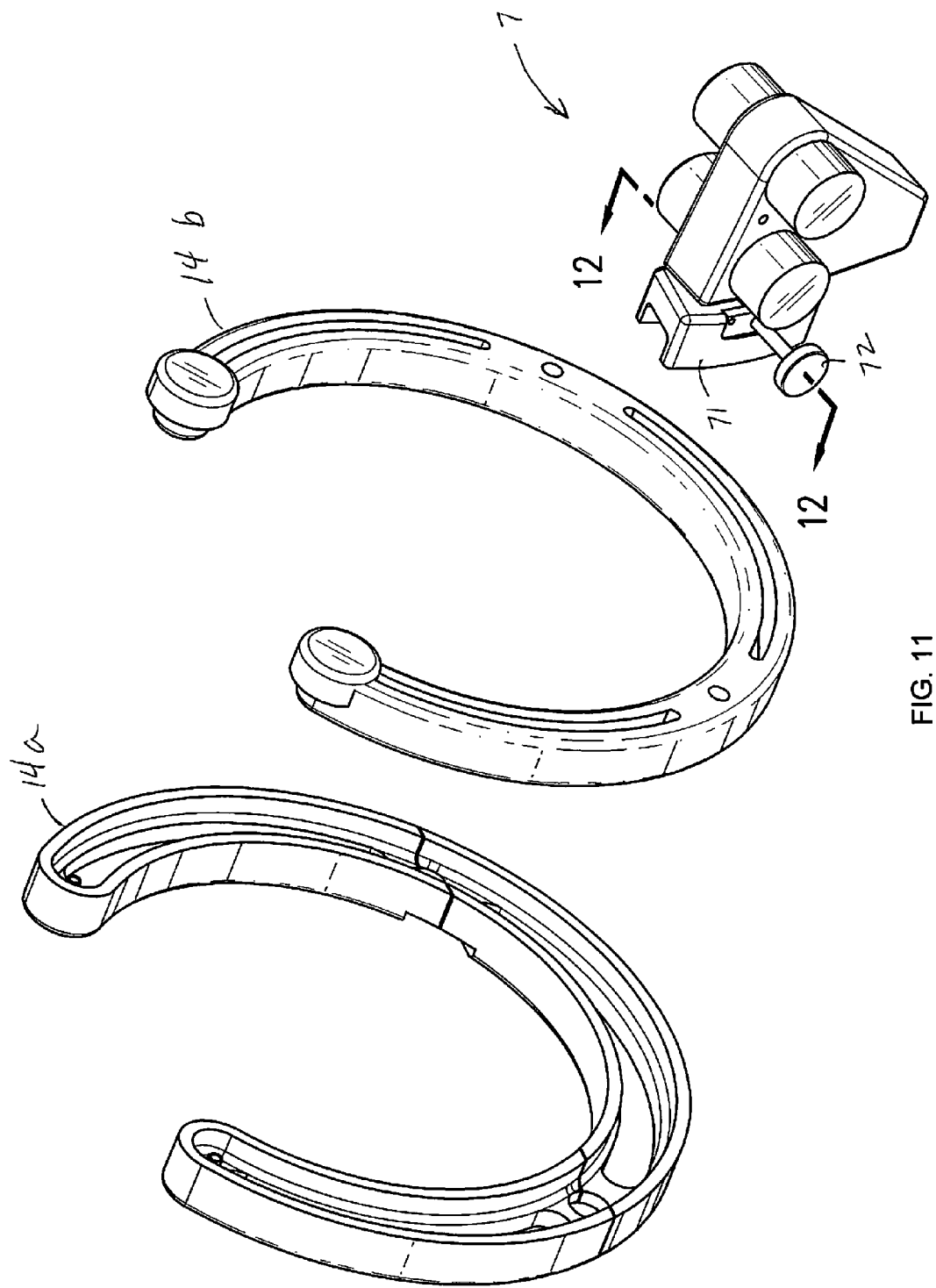
FIG. 11 is an exploded view of components of the laser support and laser mount.
Figure 12:
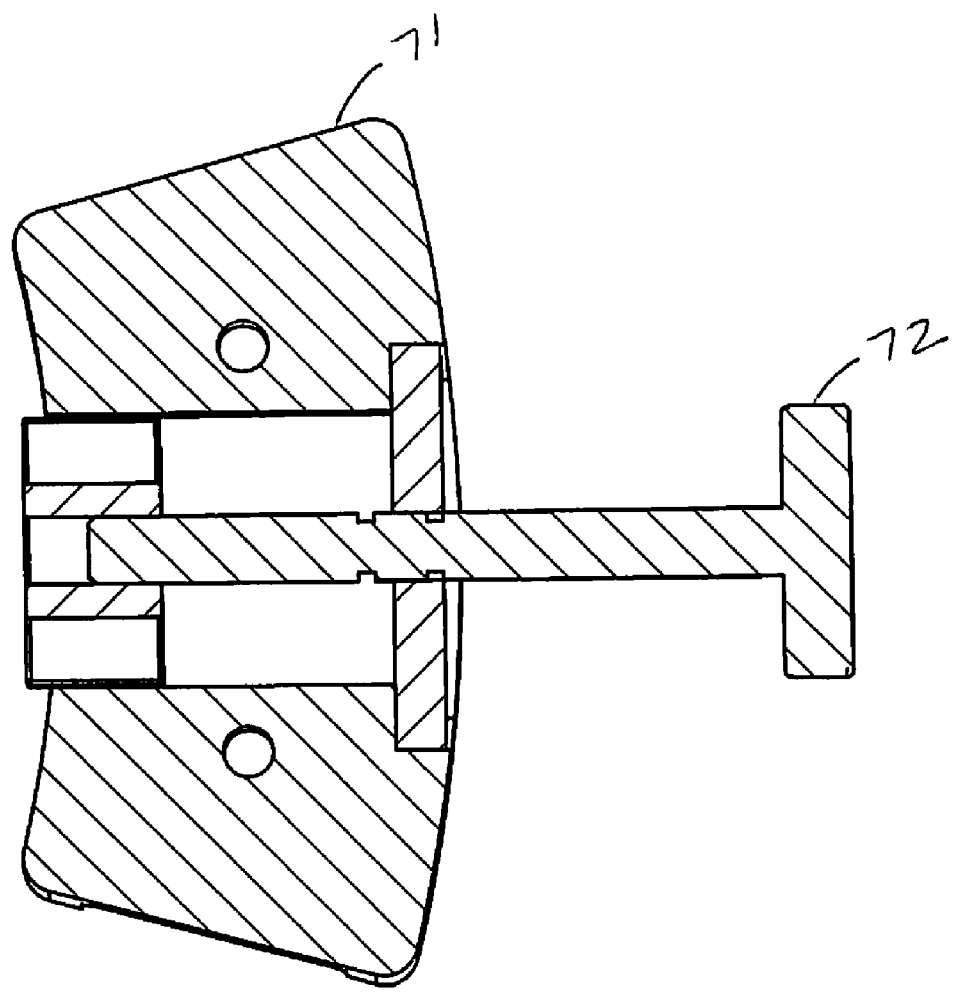
FIG. 12 is a cross-sectional view of the laser mount along line 12-12 of FIG. 11.

FIG. 2 illustrates a laser support 14 with a track 23 to which five laser housings 9 are attached. A first laser support portion 14a and a second laser support portion 14b cooperate to form track 23. Each laser housing 9 has a laser mount 7 which cooperates with track 23 to enable the lasers to move along the perimeter of the bore in the track 23. FIGS. 11 and 12 show laser mount 7 (laser housing 9 is not shown). The laser mount 7 comprises a bracket 71 which rides along track 23, preferably in a grooved channel. The laser mount 7 can be secured at desired locations around the bore using a spring-loaded clamp 72. To accommodate arms of different sizes, the laser mount 7 also has a t-groove or dovetail groove that allows the laser mount 7 to be moved in a direction perpendicular to a diameter of the laser support 14. This groove is oriented to point the lasers to the center of the bore. This allows a distance-from-the-arm adjustment. Preferably the laser energy sources emit laser energy substantially within the bore and in a direction substantially parallel to the plane of the laser support 14, in emissions similar to the spokes of a wheel. See FIGS. 3A-C. In other words, preferably each laser housing 9 is secured in place such that each laser energy source 11 emits laser energy in a plane substantially perpendicular to the axis of the bore, such that energy is directed to the center of the body part being treated. The emissions may deviate from the plane of the laser support 14 if desired.

The laser energy sources 11 may be any source suitable for low-level laser therapy. It has been shown that low-level laser therapy can be effective throughout the visible, near infrared and near ultraviolet regions. Laser diodes are currently available to cover only a limited part of the available spectrum, so other laser energy sources may be used. To obtain maximum benefit it may be desirable to stimulate the patient at two or more different wavelengths. The laser energy sources may each emit the same wavelength of laser light as the others, or the laser energy sources may emit different wavelengths of laser light. Persons skilled in the art will be aware that various laser energy sources are known in the art for use in low-level laser therapy. They include Helium-Neon lasers having a 632 nm wavelength and semiconductor diode lasers with a broad range of wavelengths between 600-800 nm. The laser energy source in the preferred embodiment is a semiconductor laser diode that produces light in the red range of the visible spectrum, having a wavelength of about 635 nm. Other suitable wavelengths are used for other particular applications. While many low-level laser therapy regimen include ultraviolet or infrared laser light, it is advantageous to utilize at least one laser beam in the visible energy spectrum so that the operator can see the laser light as it impinges the patent's body and the area treated can be easily defined. The preferred laser energy sources 11 emit less than one watt of power each. Diodes of various other wattages may also be employed to achieve the desired laser energy for the given regimen.

In the preferred embodiment, the laser light is a continuous beam. Alternatively, the laser light may be pulsed. Pulse duration controllers are connected to the laser energy sources 11 to form a control circuit that controls the duration of each pulse of laser light emitted, referred to herein as the pulse width. Pulse widths from 0 to 100,000 Hz may be employed to achieve the desired treatment effect without adversely affecting the patient's tissue. For fat reduction, the treatment goal is to deliver laser energy to the fatty area while avoiding damage to adjacent tissue or laser-induced sensation in the patient's nerves. The controls 15 used to control the laser housings 9 and laser energy sources 11 are described in more detail below.

For treating cellulite or contouring the body using low-level laser light, laser energy is applied to targeted areas of cellulite on a patient's body. The targeted areas of cellulite are made up of adipocyte tissue below the skin of the patient. Sufficient laser energy is applied to the adipocyte tissue through the skin to release at least a portion of the intracellular fat into the interstitial space. The released intracellular fat is then removed from the body through the body's normal systems, such as metabolic, lymphatic, or excretory systems. The procedure may be repeated in one or more additional areas to remove additional cellulite. Moreover, the procedure may be repeated one or more times at each targeted area over a period of days or weeks. The procedure reduces fat as well as cellulite.

Typically, fat leakage into the interstitial space is seen as early as 3-5 minutes of laser energy application. The preferred treatment is about 20 minutes of laser energy application, three times a week for about two weeks. Alternatively, the application of twenty minutes of laser energy can be repeated over longer or shorter time periods, such as repeated treatments within forty-eight hours. The dosage of laser energy required to achieve release of the intracellular fat into the interstitial space will vary depending on the thickness of the patient's skin, thickness of fatty tissue, and other biological factors peculiar to each patient.

The mechanism involved in releasing the intracellular fat from the cells is believed to be the formation of a transitory pore in the cell membrane. Adipose tissue comprises normal fat cells wherein the cell membrane is filled with intracellular fat. Upon sufficient doses of low-level laser energy, the cell membrane is momentarily disrupted, releasing the intracellular fat. Upon cessation of the energy application, the pores close and the cell membrane returns to contiguity. The fat cell is not destroyed, provided the duration of laser treatment is appropriate. For a 635 nm laser of less than 1 W, treatments of less than about 12 minutes do not destroy cells.

Applying low level laser energy causes no immediate detectable temperature rise of the treated tissue and no macroscopically visible changes in tissue structure. Low level laser energy penetrates the skin and is specific to the depth of the desired zone of fat to be treated. Consequently, the treated and surrounding tissue is not heated and is not damaged. Preferably the laser light is visible to the human eye so that the area of application is easily determined.

Figure 6:
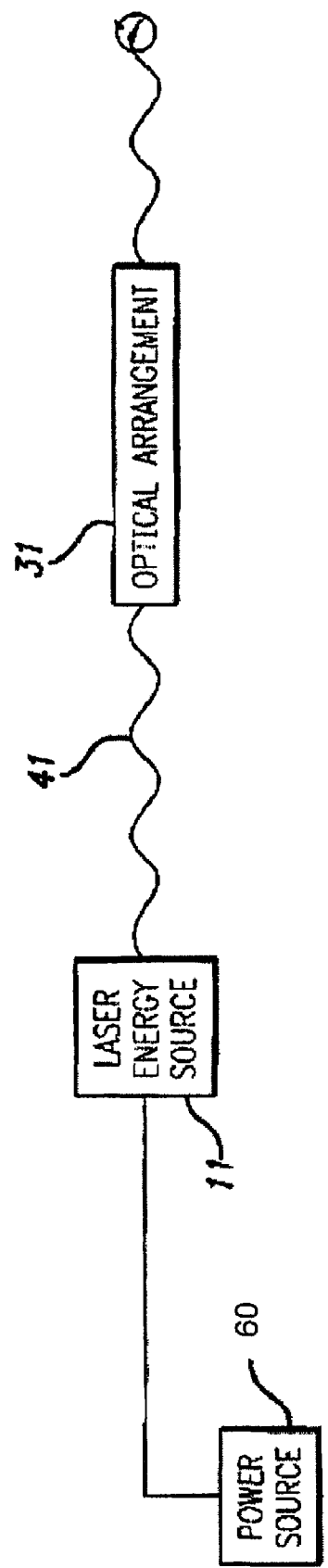
FIG. 6 is a schematic illustration of the laser emissions of the present invention.
Figure 7:
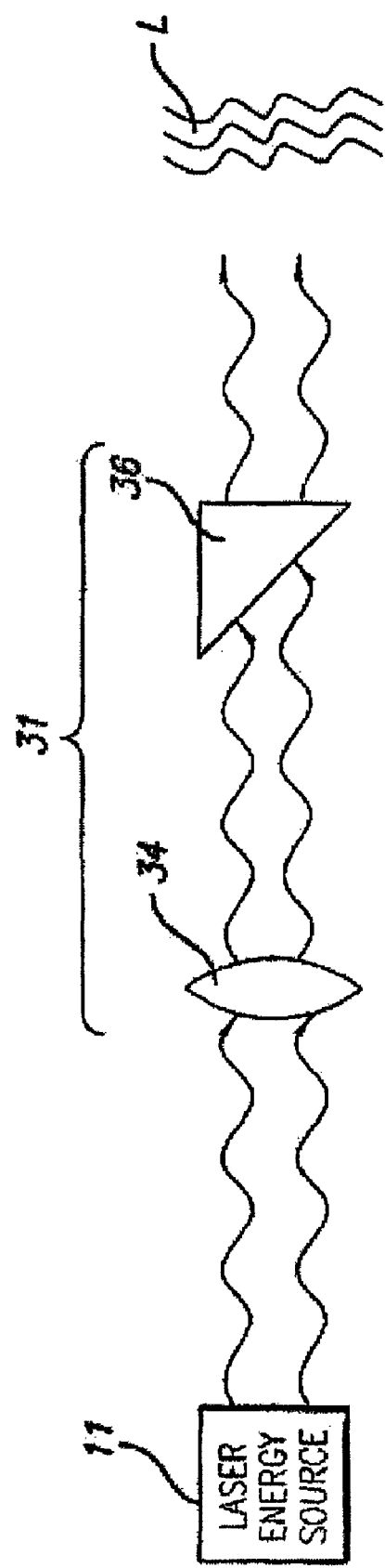
FIG. 7 is a schematic illustration of the optical arrangement of the linear spot shape of the laser emissions.

The laser device can optionally include optics for shaping the beam to create desired spot shapes, as described in U.S. Pat. No. 6,746,473 issued to Tucek and Shanks, incorporated herein by reference. In the preferred embodiment, laser energy is applied with a laser device capable of creating a linear spot shape. By using a line of laser light, the number of times the laser light must be scanned back and forth across the targeted area is minimized relative to a stationary single spot emission of light. FIGS. 6 and 7 are schematic illustrations of a laser device with optics for shaping the beam and creating a linear shape. The laser device includes an optical arrangement 31 having a collimating lens 34 and a line generating prism 36 disposed in serial relation to the laser energy source 11 and power source 60. The collimating lens 34 and line generating prism 36 receive and transform the generated beam of laser light into a line of laser light L. As an alternative, a suitable electrical or mechanical arrangement or combination thereof could be substituted for or combined with the optical arrangement to achieve a desired spot shape.

Each laser beam 41 exits the corresponding laser energy source 11 and is shone through optical arrangements 31 that produce beam spots of certain shapes. The beam spot is the cross-sectional shape and size of the emitted beam as it impinges the target area. For example, a laser beam of circular cross-section creates a circular beam spot as the laser light impinges the treatment area. If the laser beam is in the visible range, a circular beam spot can be seen on the treatment area of substantially the same diameter as the laser beam emitted from the laser energy source, provided the optical arrangement does not manipulate the laser beam. The laser beam can be manipulated, such as by collimation, refraction, masking, or another method of reshaping a laser beam, in order to produce beam spots of different sizes and shapes. In the preferred embodiment, the laser beams 41 are shaped to produce linear beam spots on the patient.

Each laser energy source 11 can also be a laser scanning device such as the inventions described in U.S. Published Patent Application 2006/0095099 belonging to Shanks and Tucek, which is incorporated herein by reference. By using laser scanning devices, the line generating prism can be operated to scan laser light in any pattern, as described in the U.S. Published Patent Application 2006/0095099. Parameters may be entered to program the laser energy sources in a required manner to achieve any desired laser treatment path upon the patient. The device 10 may be programmed to direct the laser output into some regions more than others so that one region may have greater treatment than another region. The scan areas of optical arrangements from multiple laser energy sources may overlap, whether they emanate from the same housing or separate housings.

Figure 8:
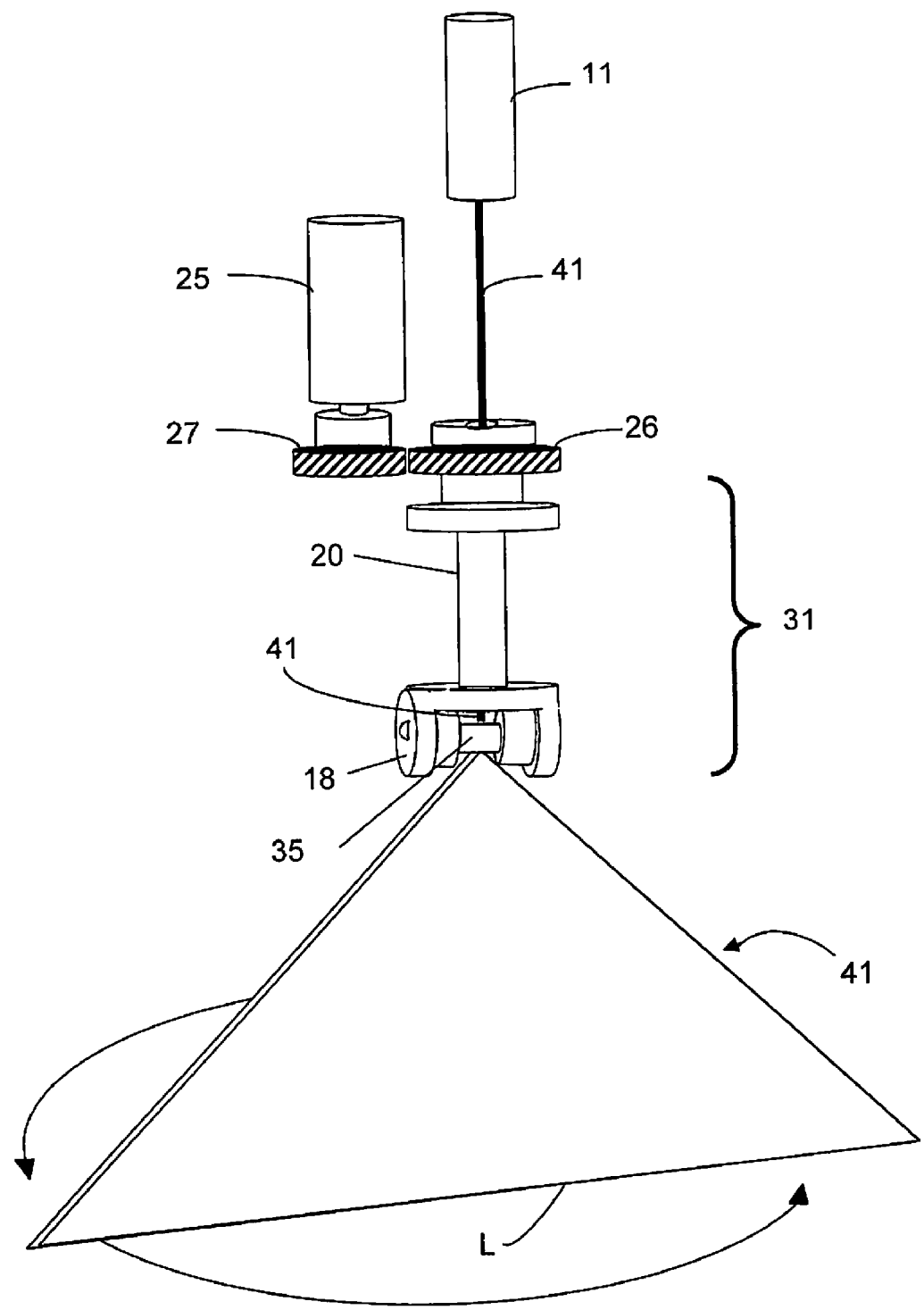
FIG. 8 is a perspective view of a scanning head optical arrangement of the present invention.
Figure 9:
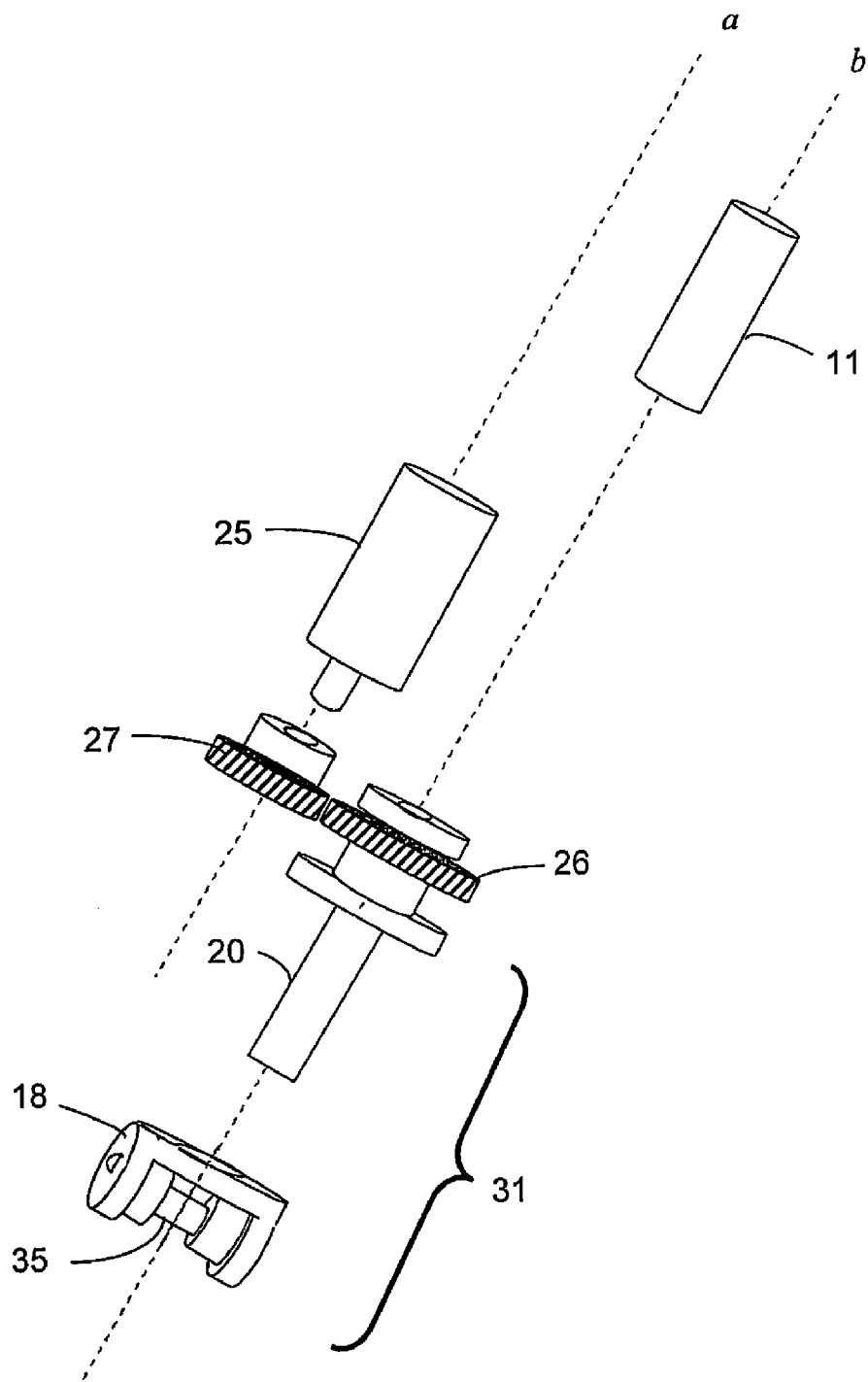
FIG. 9 is a perspective view of the scanning head of FIG. 8, exploded along axes a and b.
Figure 10:
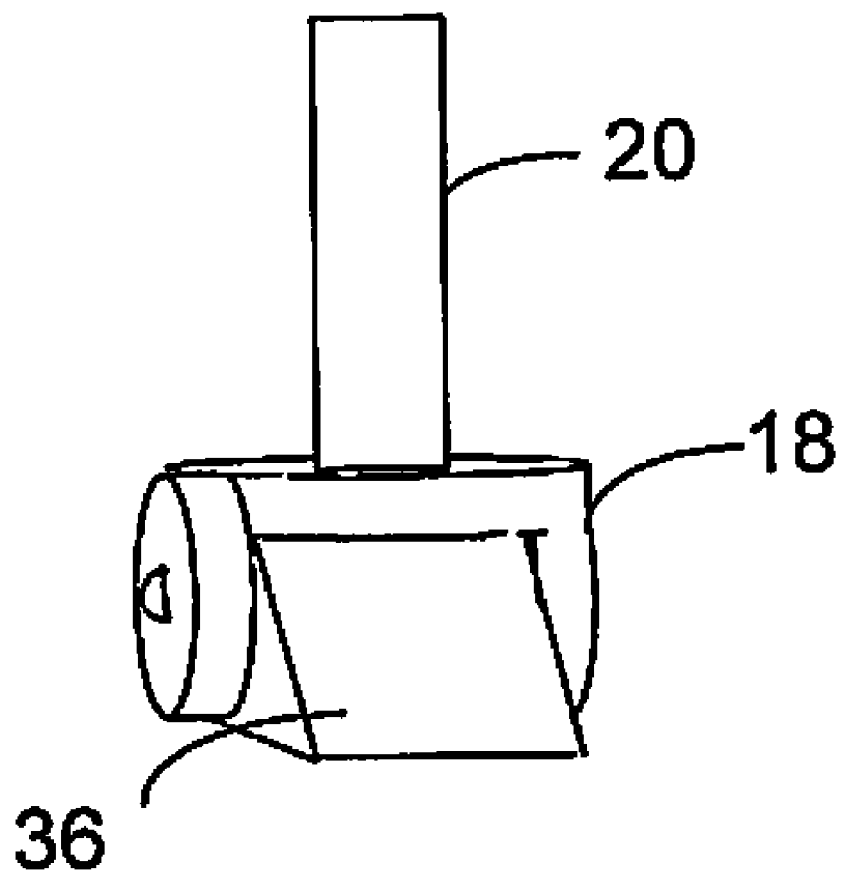
FIG. 10 is a perspective view of the universal carriage shown in FIG. 8 holding a prism instead of a rod lens.

Referring to FIGS. 8 and 9, the preferred optical arrangement 31 is a scanning head used to create a beam spot on the treatment area. To create the beam spot, the laser beam 41 emitted from the laser source 11 is directed to the scanning head, which comprises a hollow spindle 20 through which the laser beam 41 is conveyed. A rotatable carriage 18 holds an optical element upon which the laser beam 41 is incident. Preferably, the laser beam 41, spindle 20 and carriage 18 are substantially co-axial. Preferably, a linear first beam spot L with it centerpoint coaxial with the spindle 20 is generated by directing the laser beam 41 to an optical element. A rod lens 35 is preferred as the optical element, but a prism 36, as shown in FIG. 10, or other optical element or combination thereof may suffice. In other embodiments, the first beam spot may be another circular or non-circular shape, such as a filled or outlined polygon, a multi-pointed star, or a series of parallel or crossing lines. As the carriage 18 rotates, the linear beam spot L rotates too, becoming, in essence, a rotating diameter of an apparent circular second beam spot. In the preferred embodiment, when the carriage 18 is rotated through at least 180°, the linear first beam spot L sweeps through a complete circle. Preferably, the carriage 18 is rotated slowly so that the beam spots 1, 2 impinge the same treatment area in an alternating pattern. Alternatively, with electronic or computerized control, the carriage 18 may automatically rotate very quickly, causing the laser beam 41 to appear to create a substantially circular second beam spot on the patient's skin. The shape, however, is actually the result of the scanning light diameter sweeping from location to location at a speed that makes the motion nearly imperceptible to the human eye. The longer the line, the larger the beam spot.

The carriage 18 is rotated with a drive assembly. The drive assembly is preferably a main drive gear 26 which is mated with a minor drive gear 27. The minor drive gear 27 is driven by a main drive motor 25. The carriage 18 rotates around the axis as the main drive gear 26 is turned. Thus, the laser beam 41 from laser energy source 11 passes through the hollow spindle 20 and strikes an optical element which deflects the laser beam into a linear beam spot L that, in combination with the rotation, appears as a circular beam spot. Preferably, the laser beam 41 remains coaxial with the hollow spindle 20 through the optical element, so that the center of the beam spot created by the optical element is on the axis of the hollow spindle 20. The drive assembly may also be controlled by micromanipulators according to signals received from the controls 15.

The controls 15 may be constructed from discreet or integrated circuits, or a combination of both, as known in the art. In the preferred embodiment, within the controls 15, a programmable logic circuit ("PLC") electrically receives one or more input parameters related to the treatment to be performed. The input parameters may be received before, during, or after the treatment, and may be stored in the PLC as a preset treatment. The PLC uses the desired treatment parameters to control the operations of the laser housings 9 and laser energy sources 11. The operations of the laser housings 9 and laser energy sources 11 that may be controlled include: overall duration of laser emission from each laser housing 9; pulse width, variation of pulse width, and duration of each pulse width application; rotational speed and direction of carriage 18, if any; and area to scan. A voltage regulator manages power conversion to direct current, if needed, and regulates the voltage applied to the PLC, interface 16 and laser housings 9 and laser energy sources 11. Typically, this voltage management includes reducing the voltage from mains-standard 120V or 240V to 24V for the PLC and interface 16, and 5-8V to control the laser energy sources 11 and any drive motors for rotating or oscillating optical arrangements 31, 32. The voltage regulator may be a component attached to the PCB as described below, or may be integrated into the PLC.

An interface 16, configured to display treatment options to a device 10 operator and receive input from the operator, may be mounted in the stanchion 12, in electronic communication with the laser energy sources 11. Preferably the interface 16 is a touch screen. Within the interface 16, electronic components mounted on a printed circuit board ("PCB") electrically receive input parameters. The electronic components may include transistors, resistors, capacitors, conductive traces, and other components need to form a circuit configured to receive input and transmit it to the PLC. An input device is electrically connected to either the PLC or the components of the PCB, and receives the input from the operator. Preferably, the input device is attached by universal serial bus ("USB") connection to the PLC. The input device may be a keyboard, mouse, touch screen, microphone, or other input device. Preferably, the input device is an integrated touch screen that displays options to the operator and receives the operator's selections. Preferably, the interface 16 is attached with interface mounts 83 to the stanchion 12. Alternatively, the interface 16 or other combined or separate input and output devices may be remote from the stanchion 12 and receive and transmit using radio frequencies or other methods known in the art. The interface 16 may receive input, which preferably comprises treatment parameters, before, after, or during treatment.

The laser device 10 may require a key to be inserted before the device may be used. This allows usage to be monitored through key-checkout procedures, and also provides an emergency shutoff as required in the United States for certain alternating current-powered devices. The key is inserted into a keyswitch 84 mounted in a keyswitch mount near the interface 16. A socket 88 enables the device to be connected to a wall outlet for mains power. Alternatively the device can be powered by a battery.

In the preferred embodiment, the device 10 is used to reduce fat in a patient's upper arm. The patient lays prone or supine on a table and inserts her arm through the bore of laser support 14 and rests her forearm on the arm rest 54. See FIG. 4, which illustrates a patient lying on her back with her right arm inserted through the bore of laser support 14 and her forearm resting on the arm rest 54. The patient's upper arm is then treated with laser energy using a 635 nm semiconductor diode laser with maximum power of 1 W. The laser energy is applied for 20 minutes at the targeted fat areas without touching the patient. Had the patient's arm been lying on a table, only a portion of the arm could have been treated, so the patient would have had to be turned over to treat the yet-untreated portion of the arm. The present device thus reduces treatment time by half.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

We claim:

1. A laser device for applying low-level laser energy to a patient's body part, the laser device comprising:
   a. a stanchion that is adjustable in height, the stanchion having a base;
   b. a C-shaped ring through which a patient may insert the body part to be treated, the ring connected to the stanchion;
   c. a plurality of laser energy sources within a plurality of housings, the housings slidably attached to the ring, such that the lasers can be moved from one position to another around the perimeter of the ring;
   d. electronic controls in communication with the laser energy sources for independently controlling the generation of laser energy by each of the laser energy sources, the controls housed in the stanchion;
   e. a computer interface attached to the stanchion, the computer interface in communication with the electronic controls.

2. The device of claim 1 wherein the laser energy sources emit laser energy substantially simultaneously around the patient's body part.

3. The device of claim 1 wherein the stanchion is shaped to cantilever the ring over the base of the stanchion.

4. The device of claim 1 wherein each housing further comprises a laser mount which cooperates with a track to enable the lasers to move from one position to another around the perimeter of the ring.

* * * * *